United States Patent
Hasson et al.

(10) Patent No.: US 7,465,749 B2
(45) Date of Patent: Dec. 16, 2008

(54) LETROZOLE PURIFICATION PROCESS

(75) Inventors: Michal Hasson, Beer Sheva (IL); Hila Isenberg, Gedera (IL); Efrat Manoff, Lehavim (IL); Moshe Bentolila, Moshav Tekoma (IL); Oded Friedman, Yehiel (IL); Lior Zelikovitch, Mazkeret Batya (IL)

(73) Assignee: Chemagis, Ltd., Bnei Brak (IL)

( * ) Notice: Subject to any disclaimer, the term of this patent is extended or adjusted under 35 U.S.C. 154(b) by 0 days.

(21) Appl. No.: 11/498,677

(22) Filed: Aug. 3, 2006

(65) Prior Publication Data

US 2007/0112203 A1    May 17, 2007

Related U.S. Application Data

(63) Continuation-in-part of application No. 11/273,276, filed on Nov. 14, 2005.

(51) Int. Cl.
*A61K 31/4196* (2006.01)
*C07D 249/08* (2006.01)

(52) U.S. Cl. .................................. 514/383; 548/262.2
(58) Field of Classification Search ................. 514/383
See application file for complete search history.

(56) References Cited

U.S. PATENT DOCUMENTS

| 4,978,672 A | 12/1990 | Bowman et al. |
| 5,073,574 A | 12/1991 | Lang |
| 5,378,721 A | 1/1995 | Lang |
| 5,473,078 A | 12/1995 | Bowman et al. |
| 2006/0128775 A1 | 6/2006 | Patel et al. |

FOREIGN PATENT DOCUMENTS

| CN | 1754876 A | 4/2006 |
| WO | WO 2004/076409 A2 | 9/2004 |
| WO | WO 2005/047269 A1 | 5/2005 |

*Primary Examiner*—Kamal A Saeed
*Assistant Examiner*—Shawquia Young
(74) *Attorney, Agent, or Firm*—Leydig, Voit & Mayer, Ltd.

(57) ABSTRACT

Provided is a process for purifying a letrozole product that contains an isoletrozole impurity, which process preferably includes converting at least a portion of the isoletrozole impurity into 4,4'-dicyanobenzophenone and removing 4,4'-dicyanobenzophenone, to produce a purified letrozole product.

21 Claims, No Drawings

LETROZOLE PURIFICATION PROCESS

CROSS-REFERENCE TO RELATED APPLICATIONS

This patent application is a continuation-in-part of copending U.S. patent application Ser. No. 11/273,276, filed Nov. 14, 2005.

BACKGROUND OF THE INVENTION

Letrozole, the active ingredient in the product Femara®, is a nonsteroidal aromatase inhibitor, which has the chemical name 4-[α-(4-cyanophenyl)-1-(1,2,4-triazolyl)-methyl]-benzonitrile, and the following structural formula (I):

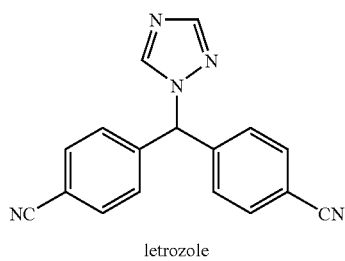

letrozole

Letrozole was developed for treatment of advanced breast cancer in postmenopausal women with disease progression following anti-estrogen therapy, especially for first-line treatment of postmenopausal women with hormone receptor positive or hormone receptor unknown locally advanced or metastatic breast cancer.

The endosynthesis of estrogen in postmenopausal women is mediated by the aromatase enzyme, which converts androstenedione and testosterone and other androgens into estradiol and estrone. Letrozole inhibits the biosynthesis of estrogen from adrenal androgens (thus causing reduction in estrogen levels) by competitive binding to the heme portion of the cytochrome P450 subunit of aromatase. This binding reduces estrogen production, which significantly lowers serum estrogens. The suppression of estrogen may decrease the stimulatory effects of estrogen on tumor growth in estrogen-responsive tumors. Letrozole reportedly exerts no clinically relevant detectable effect on the synthesis of adrenal corticosteroids and aldosterone or on thyroid function.

U.S. Pat. No. 4,978,672 ("the '672 patent") describes a process for preparing letrozole by reacting α-bromo-4-tolunitrile with 1,2,4-triazole to produce 4-[1-(1,2,4-triazolyl) methyl]-benzonitrile, and reacting the product with 4-fluorobenzonitrile to obtain letrozole.

U.S. Pat. No. 5,473,078 ("the '078 patent") describes a method for preparing 4-[1-(1,2,4-triazolyl)methyl]benzonitrile by refluxing a solution of c-bromo-4-toluinitrile with 1,2,4-triazole for 15 hours in a mixture of acetonitrile and chloroform. The intermediate is purified by chromatography on silica gel, eluting with chloroform and isopropanol, and then reacted with 4-fluorobenzonitrile and potassium tert-butoxide in DMF, to obtain letrozole. An exemplary process described in the '078 patent is generally depicted in Scheme 1.

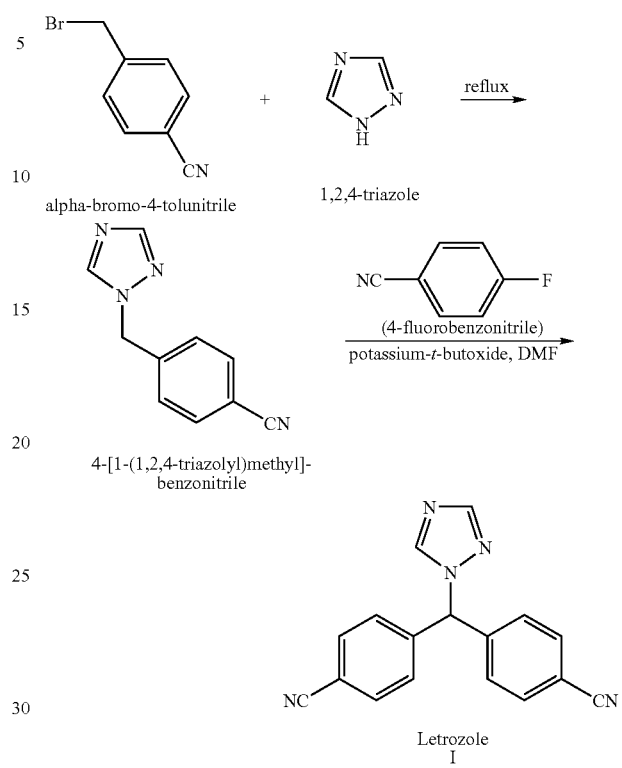

Scheme 1

The processes described in the '672 and '078 patents are problematic in that the first step produces considerable quantities of the undesired isomer 4-[1-(1,3,4-triazolyl)-methyl]-benzonitrile, which has the following structural formula (II):

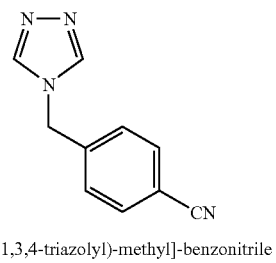

4-[1-(1,3,4-triazolyl)-methyl]-benzonitrile

Methods for addressing the problem of forming the 1,3,4-isomer (II) have been reported. For instance, application WO 2005/047269 describes a precipitation process for separating the desired intermediate (4-[1-(1,2,4-triazolyl)methyl]-benzonitrile) from the 1,3,4-isomer (II). However, this method requires an extra step of purification at an intermediate stage in the synthesis, which can be impractical on an industrial scale.

International patent application WO 2004/076409 ("the '409 application") describes a regioselective process for preparing letrozole, which includes reacting 4-halomethyl-benzonitrile with 4-amino-1,2,4-triazole followed by deamination and reaction with 4-fluorobenzonitrile. The process described in the '409 application is generally depicted in Scheme 2.

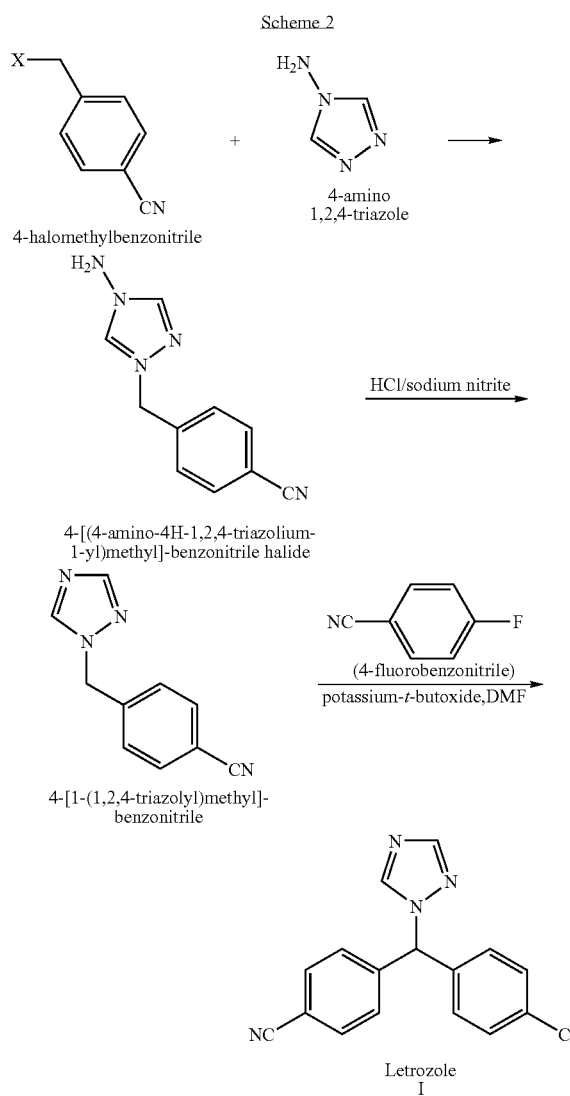

Scheme 2

The '409 application teaches that the process described in the '672 patent produces the unwanted isomer of formula II (20-40%) in the first step, and upon treating the product with 4-fluoro-benzonitrile, produces letrozole and 4-[α-(4-cyanophenyl)-1-(1,3,4-triazolyl)methyl]-benzonitrile (hereinafter "isoletrozole"), which has the structural formula (III):

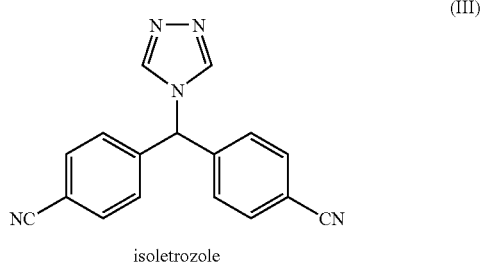

isoletrozole

While the process described in the '409 application is said to avoid formation of the unwanted isomers (II) and (III), the synthetic route requires an additional step of deamination with sodium nitrite and hydrochloric acid. Further, reacting sodium nitrite with hydrochloric acid produces nitrous acid, which is toxic and can create an explosion hazard. As such, the process described in the '409 application has limited potential for industrial application.

There is a need for an improved, industrially viable process for the large scale preparation of highly pure letrozole. The present invention provides such a process.

BRIEF SUMMARY OF THE INVENTION

It has been surprisingly discovered that the impurity isoletrozole is more rapidly oxidized than letrozole and that the oxidation product, 4,4'-dicyanobenzophenone (V), is easily separable from letrozole, e.g., by crystallization, such that highly pure letrozole can be obtained while avoiding the need to physically separate isoletrozole. In one embodiment, the present invention provides a process for purifying a letrozole product that contains an isoletrozole impurity, which process includes converting at least a portion of the isoletrozole impurity into 4,4'-dicyanobenzophenone, e.g., via oxidation, and removing 4,4'-dicyanobenzophenone, to produce a purified letrozole product.

The method of the present invention can be used for purifying letrozole obtained by processes that generate isoletrozole as an impurity. An exemplary process of the present invention includes reacting bromo-bis-(4-cyanophenyl)-methane with triazole in a solvent and in the presence of a base to produce a letrozole product containing an isoletrozole impurity; reducing the content of at least a portion of the isoletrozole, e.g., by selective oxidation, to produce 4,4'-dicyanobenzophenone; and optionally purifying the letrozole thus obtained by selective precipitation from the reaction mixture as described herein (e.g., by adding a mixture of water and a water-miscible solvent) and/or by crystallization, to remove (e.g., separate) at least a portion of the 4,4'-dicyanobenzophenone.

Letrozole containing low levels of isoletrozole can thus be obtained using the method of the present invention. Preferably, the letrozole purified in accordance with the present invention contains about 10% isoletrozole or less (as determined by HPLC), preferably less than about 10% isoletrozole (as determined by HPLC).

It is believed that the compound 4,4'-dicyanobenzophenone is produced by the oxidation of both letrozole and isoletrozole. As noted above, however, it has been found that isoletrozole is oxidized faster than letrozole. It has been discovered by the inventors of the present invention that the conversion reaction can be achieved by air oxidation. In a preferred embodiment, the conversion reaction is carried out by bubbling air into the reaction mixture until the content of isoletrozole is below about 10% (as determined by HPLC), which allows highly pure letrozole to be obtained on large scale via re-crystallization from methanol.

Table 2 depicts the amounts of letrozole and isoletrozole obtained (according to HPLC) in different production experiments carried out under the same production conditions, which included bubbling air into the reaction mixture upon completion of the synthesis reaction, withdrawing samples of the reaction mixtures and analyzing samples by HPLC before and after air bubbling. Although the letrozole content at the end of the reaction with air bubbling in experiments 5 and 6 is over 80%, the content of isoletrozole is higher than 10% and multiple re-crystallizations from methanol were needed to obtain a highly pure product.

Preferably, the impeller speed during the oxidation is at least about 500 RPM, and more preferably from about 600 to about 800 RPM. A "pump down" impeller configuration has been used in experiment No. 3 at 600 RPM, which required a longer air bubbling time of 30 minutes to lower the content of isoletrozole and 10 hours were needed to complete the reaction. However, when a "pump up" impeller configuration has been used in experiment No. 4 at 700 RPM with longer air bubbling time of 30 minutes, a low yield of 50% of letrozole was obtained, which is believed to have been caused by over oxidation. Preferably, the air bubbling time ranges from about 1 minute to about 30 minutes, e.g., about 15 minutes. The oxidation reaction is preferably carried out at a temperature of from about 25° C. to about 100° C., e.g., about 80° C.

DETAILED DESCRIPTION OF THE INVENTION

The present invention provides an improved process for obtaining letrozole in high purity without column chromatography. The process of the present invention preferably includes purifying a letrozole product that contains an isoletrozole impurity by converting at least a portion of the isoletrozole impurity into 4,4'-dicyanobenzophenone and removing (e.g., separating) 4,4'-dicyanobenzophenone, to produce a purified letrozole product. Preferably, the conversion of isoletrozole into 4,4'-dicyanobenzophenone is carried out by oxidizing isoletrozole. In one embodiment, the isoletrozole is oxidized by contacting isoletrozole with air.

The 4,4'-dicyanobenzophenone can be removed by crystallization, extraction, precipitation, or a combination thereof. In one embodiment, the 4,4'-dicyanobenzophenone is removed by selectively crystallizing letrozole. Preferably, the letrozole is crystallized from an organic solvent, e.g., methanol.

The letrozole product purified in accordance with the present invention preferably contains about 10% isoletrozole or less (as determined by HPLC), and more preferably less than about 10% isoletrozole (as determined by HPLC).

The method of the present invention can be used for purifying letrozole obtained by processes that generate isoletrozole as an impurity. Preferably, the method of the present invention includes, e.g., reacting an activated bis-(4-cyanophenyl)-methane with a triazole to produce letrozole containing an isoletrozole impurity; converting at least a portion of the isoletrozole impurity into 4,4'-dicyanobenzophenone; and removing (e.g., separating) 4,4'-dicyanobenzophenone, to produce a purified letrozole product. Preferably, the activated bis-(4-cyanophenyl)-methane comprises a leaving group, which can be displaced by the triazole, to produce letrozole. Suitable activated bis-(4-cyanophenyl)-methane intermediates can include, e.g., halo-bis-(4-cyanophenyl)-methane derivatives (wherein the leaving group is a halogen) and sulfonate esters of bis-(4-cyanophenyl)-methanol (wherein the leaving group is a sulfonate ester).

Exemplary methods of preparing letrozole can include reacting a triazole with an activated bis-(4-cyanophenyl)-methane of the formula (IV):

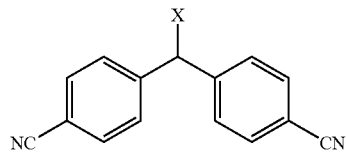

wherein X is a leaving group, to produce letrozole. Suitable leaving groups can include, for example, halogens (e.g., chloride, bromide, and the like) and sulfonate esters (e.g., methanesulfonate, p-toluene sulfonate, and the like).

Preferably, the activated bis-(4-cyanophenyl)-methane is a halogenated bis-(4-cyanophenyl)-methane. Such compounds can be produced, e.g., by halogenating bis-(4-cyanophenyl)-methanol (e.g., a compound of formula IV, wherein X is OH) or a suitable analog thereof to produce a compound of formula IV, wherein X is a halogen. For instance, the activated bis-(4-cyanophenyl)-methane can be produced by brominating bis-(4-cyanophenyl)-methanol to produce bromo-bis-(4-cyanophenyl)-methane (hereinafter BBCM).

The triazole can include, e.g., 1,2,4-triazole, a salt thereof (e.g., a metal salt of the triazole such as, e.g., 1,2,4-triazole sodium salt), or a precursor of 1,2,4-triazole, which is capable of displacing the leaving group.

The process for converting the isoletrozole into 4,4'-dicyanobenzophenone (V) is preferably carried out by selective oxidation. As indicated above, the inventors of the present invention have surprisingly discovered that isoletrozole is more rapidly oxidized than letrozole and that it is easier to separate the oxidation product, i.e., 4,4'-dicyanobenzophenone, by crystallization than it is to separate isoletrozole. The compound 4,4'-dicyanobenzophenone is believed to be the product of oxidation of both letrozole and isoletrozole (although isoletrozole is oxidized faster than letrozole as noted above). In order to demonstrate the selectivity of the oxidation, 3 parallel oxidation experiments have been carried out, using the same reaction conditions, wherein the starting material was either letrozole, isoletrozole, or BBCM. The starting material, i.e., letrozole, isoletrozole, or BBCM was stirred in an aerated solution containing toluene and DMF. The temperature in the reaction vessel was raised to 60° C. (at which clear solution was obtained) followed by addition of potassium carbonate. Samples (about 5 drops) were withdrawn approximately every hour and measured by means of HPLC.

In a preferred embodiment, the oxidation, e.g., as carried out by air bubbling, is carried out until the content of isoletrozole is below about 10% (as determined by HPLC), in which case highly pure letrozole can be obtained on large scale by re-crystallization from methanol.

Tables 1 and 2 depict the impact of oxidation on the reaction mixture, wherein the content of isoletrozole, which is not easily separable from letrozole, is reduced while the content of 4,4'-dicyanobenzophenone is increased upon reaction completion. After precipitating the impurities, e.g., 4,4'-dicyanobenzophenone and residual isoletrozole, the purity of the obtained letrozole is increased. (Crude letrozole was obtained in 98.5% purity by precipitation after air bubbling whereas crude letrozole was obtained in 96% purity by precipitation without air bubbling.)

An exemplary process of the present invention is generally depicted in Scheme 3.

Scheme 3

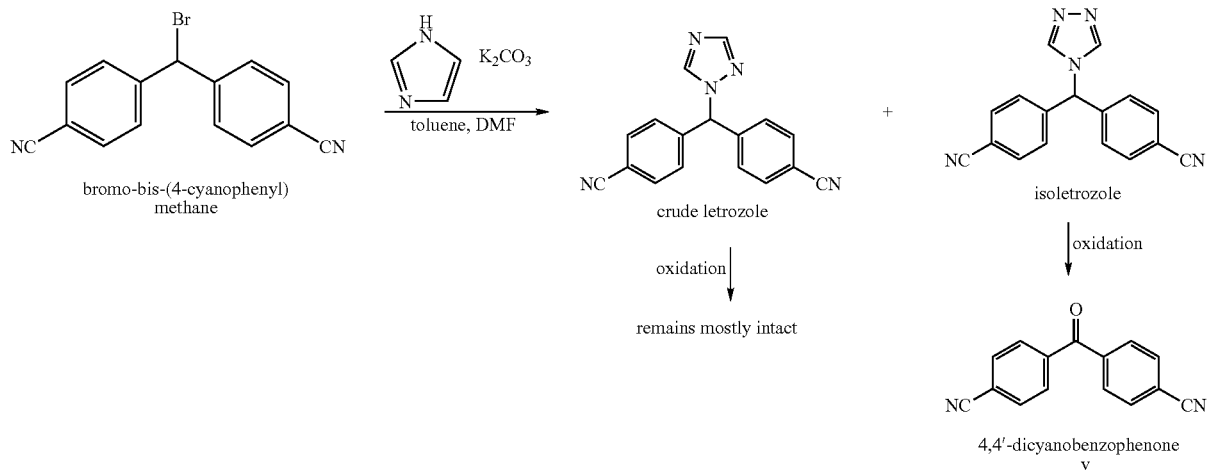

Another exemplary process of the present invention includes:

reacting bromo-bis-(4-cyanophenyl)-methane with triazole in a solvent and in the presence of a base to obtain letrozole;

reducing the content of isoletrozole, which is formed in the reaction, by selective oxidation; and optionally purifying the letrozole thus obtained by selective precipitation from the reaction mixture as described herein (e.g., by adding a mixture of water and a water-miscible solvent) and/or by crystallization.

The reaction with a triazole can be performed in any suitable solvent, which can include, e.g., toluene, ethyl benzene, xylenes, N,N-dimethylformamide (DMF), N,N-dimethylacetamide (DMA), dimethyl sulfoxide (DMSO), and combinations thereof. More preferably, the solvent used in the displacement reaction is toluene, DMF, or a combination thereof. An exemplary solvent includes a mixture DMF and toluene, e.g., in a ratio of about 2:3 DMF:toluene (vol./vol.).

Any suitable base can be used in the reaction with triazole. Suitable bases can include, e.g., sodium hydroxide, potassium hydroxide, sodium carbonate, potassium carbonate, sodium bicarbonate, potassium bicarbonate, and the like, and combinations thereof. Preferably, the base includes potassium carbonate.

The crude letrozole can be purified by any suitable process, which preferably includes selective precipitation, e.g., in the presence of at least two liquid phases, or crystallization from a solvent, as described herein.

Preferably, the letrozole product is produced by a process that produces isoletrozole as the major by-product. Letrozole and isoletrozole are structurally similar, have similar physical properties, e.g., pKa, and are not readily separable from each other using conventional extraction techniques, although the present inventors have discovered, as described in copending U.S. patent application Ser. No. 11/273,276, that the letrozole can be readily separated from the isoletrozole by selectively precipitating and/or crystallizing the letrozole, which also allows for facile purification of the letrozole.

Re-crystallization of letrozole is sufficient to obtain highly pure product on small scale (Example 8). However, to produce letrozole in the high purity desired for large scale by re-crystallization from methanol, the isoletrozole content should be less than 10%. If the content of isoletrozole is significantly higher than 10%, then multiple re-crystallizations are needed to achieve the purity desired for large scale. The yield of 65.7% (Example 2) in comparison to 70.5% (Example 1) is believed to be due to the fact that some letrozole is also being oxidized (albeit at a slower rate). However, the crude letrozole of Example 2 is of higher purity, i.e., 98.5%, than the crude letrozole described in Example 1, i.e., 96%. Hence, reducing the content of isoletrozole prior to its separation may be more economical, even though some letrozole is consumed (e.g., about 5% as suggested in Examples 1 and 2), since the need for multiple re-crystallizations is avoided, significantly reducing the volume of solvent is needed for purification. According to Table 3, the average crystallization yield is about 85.5%, hence the yield of an exemplary process comprising, e.g., oxidation and crystallization is about 65.7×0.855=56% while the yield of a process without air oxidation but with two crystallizations is about 70.5×(0.855)$^2$=51.5%. As such, purifying letrozole in accordance with the present invention is more economical. Preferably, the conversion of isoletrozole into 4,4'-dicyanobenzophenone is carried out until the amount of isoletrozole is less than about 10% (as determined by HPLC).

Letrozole containing low amounts of impurities, e.g., isoletrozole, can thus be obtained using the process of the present invention. Preferably, the process of the present invention includes selectively oxidizing a reaction mixture containing letrozole and isoletrozole until the amount of isoletrozole in the reaction mixture is less than about 10% (as determined by HPLC) before carrying out a precipitation step.

Table 3 depicts the amounts of letrozole and isoletrozole obtained (according to HPLC) in 5 production experiments carried out under comparable conditions. Each of the 5 experiments included air bubbling upon reaction completion, wherein samples of the reaction mixture were withdrawn before and after air bubbling and analyzed by HPLC.

In some embodiments of the present invention, the impeller speed during the oxidation is at least about 500 RPM, e.g., from about 600 to about 800 RPM. A "pump down" impeller configuration can be used, e.g., as described in experiment No. 3, e.g., at 600 RPM for 30 minutes to lower the content of isoletrozole and to complete the reaction. Alternatively, a "pump up" impeller configuration can be used, e.g., as described in experiment No. 4 at 700 RPM for 30 minutes, although these conditions produced a relatively low yield (50%) of isoletrozole presumably due to over oxidation.

The oxidation reaction can be carried out, e.g., by air bubbling for from about 1 minute to 30 minutes, e.g., about 15 minutes. The oxidation can be carried out at a temperature of from about 25° C. to about 100° C., e.g., about 80° C.

Optionally, the present invention provides a selective precipitation process for purifying letrozole (e.g., as described in U.S. patent application Ser. No. 11/273,276), which process preferably includes mixing letrozole containing isoletrozole, 4,4'-dicyanobenzophenone and one or more additional impurities in an organic solvent, optionally with heating, to dissolve the letrozole; cooling to precipitate crystals of purified letrozole; isolating the crystals; optionally washing the crystals; and, optionally recrystallizing to further purify the letrozole. Suitable organic solvents for crystallizing the letrozole include, e.g., methanol, ethanol, n-propanol, isopropyl alcohol, n-butanol, sec-butanol, methyl acetate, ethyl acetate, isopropyl acetate, n-butyl acetate, isobutyl acetate, diisopropyl ether, methyl tert-butyl ether, acetonitrile, acetone, methyl ethyl ketone, diethyl ketone, methyl propyl ketone, methyl isobutyl ketone, and the like, and combinations thereof. Preferably, the solvent used for crystallizing the letrozole include methanol, ethanol, isopropyl alcohol, methyl acetate, isopropyl acetate, methyl isobutyl ketone, diisopropyl ether, and combinations thereof.

Highly pure letrozole can be obtained by subjecting letrozole to one or more (e.g., successive) crystallizations. For instance, highly pure letrozole can be obtained by subjecting the selectively precipitated product to two consecutive crystallizations from a suitable organic solvent. By way of further example, highly pure letrozole can be obtained by a process, which comprises: mixing crude letrozole with a suitable organic solvent; optionally heating to an elevated temperature to dissolve the crude letrozole; gradually cooling to produce crystals of letrozole; filtering off the crystals, washing the crystals with an organic solvent; and, optionally, recrystallizing the letrozole crystals from an organic solvent.

The selective precipitation process of the present invention can be conveniently carried out, e.g., by adding a mixture of water and a water-miscible solvent to a reaction mixture that already contains a water-immiscible solvent, a water-miscible solvent, or a mixture thereof.

The following examples further illustrate the invention but, of course, should not be construed as in any way limiting its scope.

REFERENCE EXAMPLE 1

A reactor was charged with triazole (104 g, 1.5 moles) and bromo-bis(4-cyanophenyl)methane (108 g, 0.6 mole) followed by addition of DMF (720 ml) and toluene (1080 ml), and the impeller speed was set at 800 RPM. The temperature was raised to 60° C. and potassium carbonate was added (83.5 g, 0.6 mole). Then, the temperature was raised to 80° C. and mixing was maintained at this temperature during about 1.5 hours. An aliquot was withdrawn from the reaction mixture, diluted with a mixture of water and acetonitrile and analyzed by HPLC. The letrozole content was 83%, the isoletrozole content was 11.4%, while the content of 4,4'-dicyanobenzophenone was 1.6%. After cooling to a temperature of 25° C., acetic acid (57.6 ml) was added. DMF (414 ml) and water (1760 ml) were added to the reaction mixture to form a suspension (two liquid phases and a solid inter-phase in between). After heating the suspension to 60° C. the resulting mixture was allowed to cool to 25° C. for one hour and then the mixture was cooled to 20° C. and mixed at that temperature for 2 hours. The precipitated crystals were washed with water (80 ml) and dried to obtain 120.5 g of crude letrozole in 70.5% yield, having a purity of 96% by HPLC, (containing 3.5% isoletrozole).

EXAMPLE 2

A reactor was charged with triazole (104 g, 1.5 moles) and bromo-bis(4-cyanophenyl)methane (108 g, 0.6 mole) followed by addition of DMF (720 ml) and toluene (1080 ml), and the impeller speed was set at 800 RPM. The temperature was raised to 60° C. and potassium carbonate was added (83.5 g, 0.6 mole). Then, the temperature was raised to 80° C. and mixing was maintained at this temperature during about 1.5 hours. Then, air was bubbled at the same temperature for about 15 minutes at 3500 ml/minute air flow. An aliquot was withdrawn from the reaction mixture, diluted with a mixture of water and acetonitrile and injected to HPLC. The letrozole content was 73%, the isoletrozole content was 8.7% and the content of 4.4'-dicyano-benzophenone was 16.2%. After cooling to a temperature of 25° C., acetic acid (57.6 ml) was added. DMF (414 ml) and water (1760 ml) were added to the reaction mixture to form a suspension (two liquid phases and a solid inter-phase in between). After heating the suspension to 60° C. the resulting mixture was allowed to cool to 25° C. for one hour and then the mixture was cooled to 20° C. and mixed at that temperature for 2 hours. The precipitated crystals were washed with water (80 ml) and dried to obtain 112.3 g of crude letrozole in 65.7% yield, having a purity of 98.5% by HPLC, (containing 1.2% isoletrozole).

EXAMPLES 3-7

Letrozole was prepared according to Example 2, while the selective oxidation of isoletrozole was carried out at different reaction conditions. The results are detailed in tables 1 and 2 below, wherein table 1 specifies the experimental parameters and table 2 summarizes the results of the experiments.

TABLE 1

| | Experimental parameters | | | | |
|---|---|---|---|---|---|
| Experiment (Example) No. | Impeller speed, RPM | Impeller configuration | Reaction temp. ° C. | Reaction time (hrs) | Air bubbling time, min |
| 3 | 600 | pump down | 70° C. | 10.0 | 30 |
| 4 | 700 | pump up | 80° C. | 2.0 | 30 |
| 5 | 800 | " | 80° C. | 2.5 | 1 |
| 6 | 800 | " | 70° C. | 2.5 | 15 |
| 7 | 700 | " | 80° C. | 1.5 | 10 |

TABLE 2

Analytical Results

| Experiment (Example) No | Isoletrozole content % * | letrozole, % ** | Isoletrozole content % ** | Content of V, % ** | Isoletrozole content % *** |
|---|---|---|---|---|---|
| 3 | 15.3 | 77.5 | 11.8 | 13.3 | 2.2 |
| 4 | 14.5 | 50 | 3.9 | 35.6 | 0.8 |
| 5 | 16.7 | 80.8 | 16.0 | 1.7 | 1.8 |
| 6 | 14.1 | 80.2 | 11.9 | 11.3 | 2.2 |
| 7 | 14.0 | 73 | 10.0 | 17.2 | 1.1 |

\* End of the reaction without air bubbling
\*\* End of the reaction with air bubbling
\*\*\* After precipitating isoletrozole from the reaction mixture of the reaction including air bubbling
V = 4,4'-dicyanobenzophenone

EXAMPLE 8

Crude letrozole having a purity of 97.8%, prepared according to Example 2, was crystallized from methanol in 3 consecutive experiments and the results are summarized in table 3.

TABLE 3

Crystallizations from methanol

| No. of crystallization | Purity, % | Yield, % |
|---|---|---|
| 1 | 99.4 | 85.5 |
| 2 | 99.7 | 85.5 |
| 3 | 99.9 | 85.7 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process for purifying letrozole containing an isoletrozole impurity of formula (III):

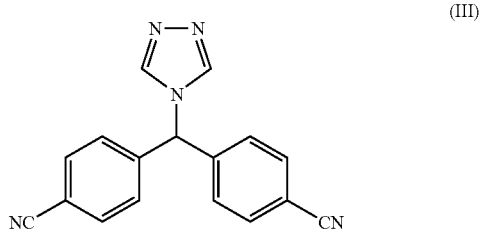

the process comprising reducing the content of isoletrozole by selectively oxidizing the isoletrozole to produce 4,4'-dicyanobenzophenone; and separating the 4,4'-dicyanobenzophenone, to produce a purified letrozole.

2. The process of claim 1, wherein the isoletrozole is air-oxidized.

3. The process of claim 1, wherein the 4,4'-dicyanobenzophenone is separated by crystallization, extraction, precipitation or a combination thereof.

4. The process of claim 3, wherein the 4,4'-dicyanobenzophenone is separated by selectively crystallizing letrozole.

5. The process of claim 4, wherein the letrozole is crystallized from an organic solvent.

6. The process of claim 5, wherein the organic solvent comprises methanol.

7. The process of claim 1, wherein the isoletrozole content is reduced to about 10% or less by HPLC after oxidation.

8. The process of claim 1, wherein the letrozole containing an isoletrozole impurity of formula (III) is produced by reacting a compound of the formula (IV):

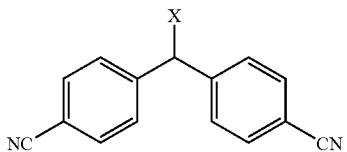

(IV)

with 1,2,4-triazole, wherein X is a halogen or a sulfonate ester, and X is displaced by the 1,2,4-triazole.

9. The process of claim 8, wherein X is a chloride or a bromide.

10. The process of claim 1, wherein the letrozole containing an isoletrozole impurity of formula (III) is produced by reacting bromo-(bis-(4-cyanophenyl))-methane with 1,2,4-triazole in a solvent and in the presence of a base.

11. The process of claim 10, wherein the solvent is toluene, ethyl benzene, a xylene, N,N-dimethylformamide (DMF), N,N-dimethylacetamide (DMA), dimethyl sulfoxide (DMSO), or a combination thereof.

12. The process of claim 11, wherein the solvent is toluene, DMF or a combination thereof.

13. The process of claim 12, wherein the DMF to toluene ratio is about 2:3 DMF:toluene (vol./vol.).

14. The process of claim 10, wherein the base is sodium hydroxide, potassium hydroxide, sodium carbonate, potassium carbonate, sodium bicarbonate, potassium bicarbonate, or a combination thereof.

15. The process of claim 14, wherein the base is potassium carbonate.

16. The process of claim 10, wherein the selective oxidation is performed by bubbling air into the reaction mixture following the reaction of bromo-bis-(4-cyanophenyl)-methane with 1,2,4-triazole.

17. The process of claim 16, wherein the air is bubbled into the reaction mixture until the content of isoletrozole is reduced to less than about 10% by HPLC.

18. The process of claim 16, wherein the oxidation is carried out at a temperature of from about 25° C. to about 100° C.

19. The process of claim 18, wherein the oxidation is carried out at a temperature of about 80° C.

20. The process of claim 10, wherein the 4,4'-dicyanobenzophenone is separated by crystallization, extraction, precipitation or a combination thereof.

21. The process of claim 20, wherein the 4,4'-dicyanobenzophenone is separated by selectively crystallizing letrozole.

* * * * *